United States Patent
Cahoon et al.

(10) Patent No.: US 6,653,531 B1
(45) Date of Patent: Nov. 25, 2003

(54) CHORISMATE SYNTHASE FROM PLANTS

(75) Inventors: Rebecca E. Cahoon, Wilmington, DE (US); Saverio Carl Falco, Arden, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/743,207

(22) PCT Filed: Jul. 20, 1999

(86) PCT No.: PCT/US99/16353

§ 371 (c)(1),
(2), (4) Date: Jan. 4, 2001

(87) PCT Pub. No.: WO00/05353

PCT Pub. Date: Feb. 3, 2000

Related U.S. Application Data

(60) Provisional application No. 60/093,611, filed on Jul. 21, 1998.

(51) Int. Cl.$^7$ ............... A01H 1/00; C07H 21/04; C07K 14/415; C12N 5/14; C12N 9/00
(52) U.S. Cl. ............... 800/295; 435/183; 435/410; 435/419; 435/252.3; 435/320.1; 530/350; 530/370; 536/23.1; 536/23.2; 536/23.6; 536/24.1; 800/278
(58) Field of Search .................. 435/183, 410, 435/419, 252.3, 320.1; 530/350, 370; 536/23.1, 23.2, 23.6, 24.1; 800/278, 295

(56) References Cited

U.S. PATENT DOCUMENTS

| | | |
|---|---|---|
| 5,187,071 A | 2/1993 | Fischer et al. |
| 5,530,186 A * | 6/1996 | Hitz et al. |

FOREIGN PATENT DOCUMENTS

| | | |
|---|---|---|
| EP | 0 608 722 A1 | 8/1994 |
| EP | 0 832 978 A2 | 4/1998 |
| WO | WO 95/33843 | 12/1995 |
| WO | WO 97/26366 | 7/1997 |
| WO | WO 98/03661 | 1/1998 |

OTHER PUBLICATIONS

National Center for Biotechnology Information General Identifier No. 2492953, Oct. 1, 2000, Gorlach, J. et al., Differential expression of tomato (*Lycopersicon esculentum* L.) genes encoding shikimate pathway isoenzymes. II. Chroismate synthase.

National Center for Biotechnology Information General Identifier No. 2492952, Oct. 1, 2000, Gorlach, J. et al., Differential expression of tomato (*Lycopersicon esculentum* L.) genes encoding shikimate pathway isoenzymes. II. Chroismate synthase.

F. Gibson, Methods Enzymol., vol. 17:362–364, 1970, Preparation of Chorismic Acid.

P.J. White et al., Biochem. Soc. Trans., vol. 15:144–145, 1987, A simple anaerobic assay for chorismate synthase.

Andreas Schaller et al., Arch. biochem. Biophys., vol. 282:437–442, 1990, Purification of Chorismate Synthase from a Cell Culture of the Higher Plant Corydalis sempervirens Pers.

Martin R. Boocock et al., FEBS Lett., vol. 154(1):127–133, 1983, Kinetics of 5–enolpyruvylshikimate–3–phosphate synthase inhibition by glyphosate.

EMBL Sequence Data Library Accession No: L33595, Jul. 11, 1994, Lim, C.O. et al., XP–002123443.

Database DBEST No: AA586083, Sep. 11, 1997, Newman, T. et al., Genes galore: a summary of methods for accessing results from large–scale partial sequencing of anonymous Arabidopsis cDNA clones.

EMBL Sequence Data Library Accession No: AA586083, Sep. 13, 1997, Newman, T. et al., Genes galore: a summary of methods for accessing results from large–scale partial sequencing of anonymous Arabidopsis cDNA clones.

Gary Millar et al., FEBS Lett., vol. 200(1):11–17, 1986, The complete amino acid sequence of 3–dehydroquinate synthase of *Escherichia coli* K12.

National Center for Biotechnology Information General Identifier No. 114181, May 30, 2000, Millar, G. et al., The complete amino acid sequence of 3–dehydroquinate synthase of *Escherichia coli* K12.

EMBL Sequence Data Library Accession No: P34002, Feb. 1, 1994, Martin, P.R. et al., Characterization of pilQ, a new gene required for the biogenesis of type 4 fimbriae in *Pseudomonas aeruginosa*.

Nicholas Nikolaides et al., Tetrahedron Lett., vol. 30(12):1461–1464, 1989, Design and Synthesis of Substrate Analogs for the Inhibition of Dehydroquinate Synthase.

John W. Frost et al., Biochemistry, vol. 23:4470–4475, 1984, Dehydroquinate Synthase from *Escherichia coli*: Purification, Cloning, and Construction of Overproducers of the Enzyme.

D. L. Pompliano et al., J. Am. Chem. Soc., vol. 111:1866–1871, 1989, Probing Lethal Metabolic Perturbations in Plants with Chemical Inhibition of Dehydroquinate Synthase.

Genbank Database DBEST No: AI065473, Jul. 24, 1998, Schutz, K. et al., Expressed sequence tags from z. mays.

EMBL Sequence Data Library Accession No: AI065473, Jul. 27, 1998, Schutz, K. et al., Expressed sequence tags from z. mays.

(List continued on next page.)

*Primary Examiner*—Phuong T. Bui

(57) ABSTRACT

This invention relates to an isolated nucleic acid fragment encoding a chorismate synthase. The invention also relates to the construction of a chimeric gene encoding all or a portion of the chorismate synthase, in sense or antisense orientation, wherein expression of the chimeric gene results in production of altered levels of the chorismate synthase in a transformed host cell.

12 Claims, No Drawings

U.S. PATENT DOCUMENTS

EMBL Sequence Data Library Accession No: AI637200, Apr. 27, 1999, Walbot, V., Maize ESTs from various cDNA libraries sequenced at Stanford University.

EMBL Sequence Data Library Accession No: AU056551, Mar. 31, 1999, Sasaki, T., Rice cDNA from mature leaf.

Markus Bischoff et al., Plant Mol. Biol., vol. 31:69–76, 1996, Cloning of a cDNA encoding a 3–dehydroquinate synthase from a higher plant, and analysis of the organ–specific and elicitor–induced expression of the corresponding gene.

EMBL Sequence Data Library Accession No: AI731017, Jun. 12, 1999, Blewitt, M. et al., ESTs from developing cotton fiber.

EMBL Sequence Data Library Accession No: AI728073, Jun. 12, 1999, Blewitt, M. et al., ESTs from developing corn fiber.

EMBL Sequence Data Library Accession No: AI489566, Mar. 17, 1999, Alcala, J. et al., Generation of ESTs from tomato carpel tissue.

Stephen Bornemann et al., Journ. of biol. Chem., vol. 270(39):22811–22815, 1995, *Escherichia coli* Chorismate Synthase Catalyzes the Conversion of (6S)–6–Fluoro–5–enolpyruvylshikimate–3–phosphate to 6–Fluorochorismate.

EMBL Sequence Data Library Accession No: C72774, Sep. 19, 1997, Sasaki, T., Rice cDNA from Panicle at flowering stage.

EMBL Sequence Data Library Accession No: AA750226, Jan. 21, 1998, Nahm, B.H. et al., Large–scale Sequencing Analysis of ESTs from Rice Immature Seed.

Andreas Schaller et al., Journ. of biol. Chem., vol. 256(32):21434–21436, 1991, Molecular Cloning and Analysis of a cDNA Coding for Chorismate Synthase from the Higher Plant *Corydalis sempervirens* Pers.

Jorn Gorlach et al., Plant Mol. Biol., vol. 23:707–716, 1993, Differential expression of tomato (*Lycopersicon esculentum* L.) genes encoding shikimate pathway isoenzymes. II. Chorismate Synthase.

EMBL Sequence Data Library Accession No.: Y14797, Sep. 12, 1997, Wind, J.C. et al., Three differentially expressed 3–deoxy–D–arabino–heptulosonate 7–phosphate synthase genes in *Morinda citrifolia*.

William E. Dyer et al., Journ. of Biol. Chem., vol. 265:1608–1614, 1990, A cDNA Encoding 3–Deoxy–D–arabino–heptulosonate 7–Phosphate Synthase from *Solanum tuberosum* L.

Jorn Gorlach et al., Plant Mol. Biol., vol. 23:697–706, 1993, Differential expression of tomato (*Lycopersicon esculentum* L.) genes encoding shikimate pathway isoenzymes. I. 3–Deoxy–D–arabino–heptulosonate 7–phsophate synthase.

James D. Jones et al., Plant Phys., vol. 108(4):1413–1421, 1995, Impaired Wound Induction of 3–Deoxy–D–arabino–heptulosonate–7–phosphate (DAHP) Synthase and Altered Stem Development in Transgenic Potato Plants Expressing a DAHP Synthase Antisense Construct.

EMBL Sequence Data Library Accession No: AI677182, May 25, 1999, Walbot, V., Maize ESTs from various cDNA libraries sequenced at Stanford University.

EMBL Sequence Data Library Accession No: AI615213, Apr. 26, 1999, Walbot, V. Maize ESTs from various cDNA libraries sequenced at Stanford University.

EMBL Sequence Data Library Accession No: AI443687, Mar. 16, 1999, Shoemaker, R. et al., Public Soybean EST Project.

EMBL Sequence Data Library Accession No: AU068686, Jun. 7, 1999, Sasaki, T. Rice cDNA from callus.

Klaus M. Herrmann, Plant Phys., vol. 107:7–12, 1995, The Shikimate Pathway as an Entry to Aromatic Secondary Metabolism.

* cited by examiner

CHORISMATE SYNTHASE FROM PLANTS

This application claims the benefit of U.S. Provisional Application No. 60/093,611, filed Jul. 21, 1998.

FIELD OF THE INVENTION

This invention is in the field of plant molecular biology. More specifically, this invention pertains to nucleic acid fragments encoding enzymes involved in chorismate biosynthesis in plants and seeds.

BACKGROUND OF THE INVENTION

Chorismate biosynthesis involves the last few steps in the common pathway for the production of the aromatic amino acids phenylalanine, tyrosine and tryptophan. The last common step of biosynthesis of aromatic amino acids produced via the shikimic acid pathway is catalyzed by chorismate synthase which produces chorismate from 5-enolpyruvylshikimate 3-phosphate. The enzyme requires reduced FMN as a cofactor. There are two forms of the enzyme described in tomato. Tomato chorismate synthase 1 and 2 have 88% identity at the amino acid level and are expressed differentially in flowers, roots and stems (Gorlach, J. and Schmid, J. (1993) *Plant Mol Biol* 23:707–716).

Manipulating either the amount or activity of this enzyme would afford manipulation of the ratio of aromatic to non-aromatic amino acids in plants, including corn, rice, soybean and wheat. This enzyme should also be useful for high throughput screening of compounds suitable for use as herbicides.

SUMMARY OF THE INVENTION

The instant invention relates to isolated nucleic acid fragments encoding chorismate synthase. Specifically, this invention concerns an isolated nucleic acid fragment encoding a chorismate synthase and an isolated nucleic acid fragment that is substantially similar to an isolated nucleic acid fragment encoding a chorismate synthase. In addition, this invention relates to a nucleic acid fragment that is complementary to the nucleic acid fragment encoding chorismate synthase.

An additional embodiment of the instant invention pertains to a polypeptide encoding all or a substantial portion of a chorismate synthase.

In another embodiment, the instant invention relates to a chimeric gene encoding a chorismate synthase, or to a chimeric gene that comprises a nucleic acid fragment that is complementary to a nucleic acid fragment encoding a chorismate synthase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a chorismate synthase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants. An additional embodiment of the instant invention concerns a method of altering the level of expression of a chorismate synthase in a transformed host cell comprising: a) transforming a host cell with a chimeric gene comprising a nucleic acid fragment encoding a chorismate synthase; and b) growing the transformed host cell under conditions that are suitable for expression of the chimeric gene wherein expression of the chimeric gene results in production of altered levels of chorismate synthase in the transformed host cell.

An addition embodiment of the instant invention concerns a method for obtaining a nucleic acid fragment encoding all or a substantial portion of an amino acid sequence encoding a chorismate synthase.

A further embodiment of the instant invention is a method for evaluating at least one compound for its ability to inhibit the activity of a chorismate synthase, the method comprising the steps of: (a) transforming a host cell with a chimeric gene comprising a nucleic acid fragment encoding a chorismate synthase, operably linked to suitable regulatory sequences; (b) growing the transformed host cell under conditions that are suitable for expression of the chimeric gene wherein expression of the chimeric gene results in production of chorismate synthase in the transformed host cell; (c) optionally purifying the chorismate synthase expressed by the transformed host cell; (d) treating the chorismate synthase with a compound to be tested; and (e) comparing the activity of the chorismate synthase that has been treated with a test compound to the activity of an untreated chorismate synthase, thereby selecting compounds with potential for inhibitory activity.

BRIEF DESCRIPTION OF THE SEQUENCE DESCRIPTIONS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Chorismate Synthase

| | | SEQ ID NO: | |
|---|---|---|---|
| Plant | Clone Designation | (Nucleotide) | (Amino Acid) |
| Corn | chpc24.pk0002.h1:fis | 1 | 2 |
| Soybean | sl1.pk0143.g5:fis | 3 | 4 |
| Wheat | wre1n.pk0094.e6 | 5 | 6 |
| Corn | csi1n.pk0050.d11:fis | 7 | 8 |
| Rice | rls48.pk0033.g1 | 9 | 10 |
| Rice | rls72.pk0029.g8 | 11 | 12 |
| Soybean | ses9c.pk001.j6 | 13 | 14 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) *Nucleic Acid Hybridisation*, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., In situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

Nucleic acid fragments encoding at least a portion of several chorismate synthases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other chorismate synthases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673; Loh et al. (1989) *Science* 243:217). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the ratio of aromatic to non-aromatic amino acids in those cells. This may also create plants that are resistant to herbicides.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptide (or portions thereof) may be produced in heterologous host cells, particularly in the cells of microbial hosts, and can be used to prepare antibodies to the these proteins by methods well known to those skilled in the art. The antibodies are useful for detecting the polypeptide of the instant invention in situ in cells or in vitro in cell extracts. Preferred heterologous host cells for production of the instant polypeptide are microbial hosts. Microbial expression systems and expression vectors containing regulatory sequences that direct high level expression of foreign proteins are well known to those skilled in the art. Any of these could be used to construct a chimeric gene for production of the instant polypeptide. This chimeric gene could then be introduced into appropriate microorganisms via transformation to provide high level expression of the encoded chorismate synthase. An example of a vector for high level expression of the instant polypeptide in a bacterial host is provided (Example 6).

Additionally, the instant polypeptide can be used as a target to facilitate design and/or identification of inhibitors of those enzymes that may be useful as herbicides. This is desirable because the polypeptide described herein catalyzes the formation of the last common precursor precursor in the biosynthesis of numerous aromatic compounds. Accordingly, inhibition of the activity of the enzyme described herein could lead to inhibition plant growth. Thus, the instant polypeptide could be appropriate for new herbicide discovery and design.

All or a substantial portion of the nucleic acid fragments of the instant invention may also be used as probes for genetically and physically mapping the genes that they are a part of, and as markers for traits linked to those genes.

Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bematzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402; Koes et al. (1995) *Proc. Natl. Acad. Sci USA* 92:8149; Bensen et al. (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptide disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| chpc24 | Corn (MBS847) 8 Day Old Shoot Treated 24 Hours With Herbicide* | Chpc24.pk0002.h1 |
| csi1n | Corn Silk** | csi1n.pk0050.d11 |
| rls48 | Rice Leaf 15 Days After Germination, 48 Hours After Infection of Strain *Magaporthe grisea* 4360-R-67 (AVR2-YAMO); Susceptible | rls48.pk0033.g1 |
| rls72 | Rice Leaf 15 Days After Germination, 72 Hours After Infection of Strain *Magaporthe grisea* 4360-R-67 (AVR2-YAMO); Susceptible | rls72.pk0029.g8 |
| ses9c | Soybean Embryogenic Suspension | ses9c.pk001.j6 |
| sl1 | Soybean Two-Week-Old Developing Seedlings | sl1.pk0143.g5 |
| wre1n | Wheat Root From 7 Day Old Etiolated Seedling** | wre1n.pk0094.e6 |

*Application of 2-[(2,4-dihydro-2,6,9-trimethyl[1]benzothiopyrano[4,3-c]pyrazol-8-yl)carbonyl]-1,3-cyclohexanedione S,S-dioxide; synthesis and methods of using this compound are described in WO 97/19087, incorporated herein by reference.
**These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer.

Example 2

Identification of cDNA Clones cDNA clones encoding chorismate synthase were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Chorismate Synthases

The BLASTX search using the EST sequences from clones listed in Table 3 revealed similarity of the polypeptides encoded by the cDNAs to chorismate synthases from *Lycopersicon esculentum* (NCBI General Identifier Nos. 2492952 and 2492953). Shown in Table 3 are the BLAST results for individual ESTs ("EST"), or the sequences of the entire cDNA inserts comprising the indicated cDNA clones ("FIS"):

TABLE 3

BLAST Results for Sequences Encoding Polypeptides Homologous to Chorismate Synthases

| Clone | Status | NCBI General Identifier No. | BLAST pLog Score |
| --- | --- | --- | --- |
| chpc24.pk0002.h1 | FIS | 2492952 | 254.00 |
| sl1.pk0143.g5 | FIS | 2492952 | 43.52 |
| wre1n.pk0094.e6 | FIS | 2492952 | 104.00 |
| csi1n.pk0050.d11 | FIS | 2492953 | 172.00 |
| rls48.pk0033.g1 | EST | 2492953 | 26.15 |
| rls72.pk0029.g8 | EST | 2492953 | 127.00 |
| ses9c.pk001.j6 | EST | 2492953 | 62.10 |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode two entire corn chorismate synthases which correspond to the two known tomato chorismate synthase isozymes (LeCS1 and LeCS2); a substantial portion of two soybean chorismate synthases; two portions of rice chorismate synthase (may be the same or different genes); and a substantial portion of a wheat chorismate synthase. These sequences represent the first corn, rice, soybean and wheat sequences encoding chorismate synthase.

Example 4

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform E. coli XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kaptonm flying disc (Bio-Rad Labs). The particles are then accelerated into the corn tissue with a Biolistic™ PDS-1000/ He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5
Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptide in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptide. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into mL of liquid medium.

Soybean embryogenic suspension cultures may then be transformed by the method of particle gun bombardment (Klein et al. (1987) *Nature (London)* 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli;* Gritz et al.(1983) *Gene* 25:179–188) and the 3' region of the nopaline synthase gene from the T-DNA of the Ti plasmid of *Agrobacterium tumefaciens.* The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 $\mu$L of a 60 mg/mL 1 $\mu$m gold particle suspension is added (in order): 5 $\mu$L DNA (1 $\mu$g/$\mu$L), 20 $\mu$l spermidine (0.1 M), and 50 $\mu$L CaCl$_2$ (2.5 M). The particle preparation is then agitated for three minutes, spun in a microfuge for 10 seconds and the supernatant removed. The DNA-coated particles are then washed once in 400 $\mu$L 70% ethanol and resuspended in 40 $\mu$L of anhydrous ethanol. The DNA/particle suspension can be sonicated three times for one second each. Five $\mu$L of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6
Expression of Chimeric Genes in Microbial Cells

The cDNAs encoding the instant polypeptide can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 $\mu$g/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 $\mu$L of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 $\mu$g/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 $\mu$L of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One $\mu$g of protein from the soluble fraction of the culture can be separated by SDS-polyacrylamide gel electrophoresis. Gels can be observed for protein bands migrating at the expected molecular weight.

Example 7
Evaluating Compounds for Their Ability to Inhibit the Activity of Chorismate Synthase The polypeptide described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant polypeptide may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptide, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptide are expressed as fusion proteins, the purification protocol may include the use of an affinity resin which is specific for the fusion protein tag attached to the expressed enzyme or an affinity resin containing ligands which are specific for the enzyme. For example, the instant polypeptide may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptide disclosed herein. Assays may be conducted under well known experimental conditions which permit optimal enzymatic activity. Assays for chorismate synthase are presented by F. Gibson (1970) *Methods Enzymol.* 17:362–364, White, P. J., Mousdale, D. M. and Coggins, J. R. (1987) *Biochem. Soc. Trans.* 15:144–145, Schaller, A., Windhofer, V. and Amrhein, N. (1990) *Arch. Biochem. Biophys.* 282:437–442 and Boocock, M. R. and Coggins, J. R. (1983) *FEBS Lett.* 154:127–133.

What is claimed is:

1. An isolated polynucleotide comprising:
   (a) a nucleotide sequence encoding a polypeptide having chorismate synthase activity, wherein the amino acid sequence of the polypeptide and the amino acid sequence of SEQ ID NO:2 have at least 90% sequence identity based on the Clustal alignment method, or
   (b) a full-length complement of the nucleotide sequence.

2. The polynucleotide of claim 1, wherein the amino acid sequence of the polypeptide and the amino acid sequence of SEQ ID NO:2 have at least 95% sequence identity based on the Clustal alignment method.

3. The polynucleotide of claim 1, wherein the nucleotide sequence comprises the nucleotide sequence of SEQ ID NO:1.

4. The polynucleotide of claim 1, wherein the amino acid sequence of the polypeptide comprises the amino acid sequence of SEQ ID NO:2.

5. A vector comprising the polynucleotide of claim 1.

6. A recombinant DNA construct comprising the polynucleotide of claim 1 operably linked to a regulatory sequence.

7. A method for transforming a cell comprising transforming a cell with the polynucleotide of claim 1.

8. A cell comprising the recombinant DNA construct of claim 6.

9. A method for producing a plant comprising transforming a plant cell with the polynucleotide of claim 1 and regenerating a plant from the transformed plant cell.

10. A plant comprising the recombinant DNA construct of claim 6.

11. A seed comprising the recombinant DNA construct of claim 6.

12. A method for isolating a polypeptide encoded by the polynucleotide of claim 1 comprising expressing the polypeptide in a cell containing a recombinant DNA construct comprising the polynucleotide operably linked to a regulatory sequence and isolating the polypeptide from the cell.

* * * * *

SEQUENCE LISTING

<160> NUMBER OF SEQ ID NOS: 14

<210> SEQ ID NO 1
<211> LENGTH: 1635
<212> TYPE: DNA
<213> ORGANISM: Zea mays

<400> SEQUENCE: 1

```
gcacgagcgc agtctcagac cctcaccaac caggcaacca aaccttctcc gatggccgcg      60
cccgtgtcgc agccgccggt gtccgccagg gcgtccacac ggtttctccc ccgcgggata     120
ggcgcgctcc cggagtccgc ccccacgtcc ctccggttat ccgtcggccg ccgtcgccgc     180
gcctccagcc tagaggtgaa ggcatcagga aatgtgttcg ggaactactt ccaggttgca     240
acctatggcg aatcccatgg aggggtgtt ggttgcgtta tcagtggctg cccacccaga      300
attcctctca ctgaggcaga catgcaagta gaactcgata gaagacgtcc gggtcaaagt     360
agaattacaa ccccaagaaa ggagactgat acatgcaaaa ttctatcagg gacacatgat     420
gggatgacta ctggtacacc aattcacgtc tttgtcccaa acacagatca aagggtggt      480 gattacagtg aaatgtctaa ggcgtacaga ccatcccatg cagatgcaac ctatgacttc     540
aagtatggag ttagagctgt gcaggaggt ggaaggtcat cagccagaga aaccattggc      600
agggtggctg caggagctct tgcaaagaaa attctaaagc tcaaatcagg agtggagatc     660 ttggcattttg tttctaaagt gcaccaagtc gtacttccag aagatgcagt tgattatgag     720
actgtaacct tggaacatat agagagcaac atcgttagat gtcctgatcc agaatatgca     780
gagaagatga ttgctgccat tgatacggta cgagttagag gagattcaat tggtggggtc     840
gtcacatgca ttgcaagaaa tgttcctcgt ggtcttggct ctcctgtttt tgacaaactt     900
gaagctgaac tggcaaaagc catgctttct cttcctgcaa gcaagggggtt tgagattggc     960 agtgggttcg ctggtacgga ctttactgga agtgagcata atgatgagtt ctatatggat    1020
gaggctggaa atgtgaggac acgaactaat cgctcaggcg gtgttcaggg agggatatca    1080
aatggtgaaa ttatttactt caagtggct tttaagccaa cagcaactat cggaaagaag     1140
caaaatactg tgtcaaggga gcatgaggat gttgaacttt tggcaagggg gcgccatgac    1200
ccctgtgttg tccctcgagc tgttcctatg gtggaatcca tggctgcgct ggtcctgatg    1260
```

-continued

```
gaccagctca tggcgcatat tgcccagtgt gagatgtttc cgctgaacct tgccctacaa   1320
gagcccattg gctctgctag cagtgcatct gaactgtcac caaacctatc ataatgtttg   1380
tcgtggaaca tgtcccagct ttccttctat cgaaattctg gtctttgcta agcagtttgc   1440
aattcggaac ccccataaac cctcgactat tgtacctaga gataaagtga acggatatca   1500
agatagaaat gcattaatgt ttttgtgatg tgtagtataa ctgatattta cccctttttct   1560 ttttttgaga gaggacgcat gatgtcgttt gagcaataaa gtttaatttg ggagaaaaaa   1620
aaaaaaaaaa aaaaa                                                    1635
```

<210> SEQ ID NO 2
<211> LENGTH: 440
<212> TYPE: PRT
<213> ORGANISM: Zea mays

<400> SEQUENCE: 2

```
Met Ala Ala Pro Val Ser Gln Pro Pro Val Ser Ala Arg Ala Ser Thr
  1               5                  10                  15

Arg Phe Leu Pro Arg Gly Ile Gly Ala Leu Pro Glu Ser Ala Pro Thr
                 20                  25                  30

Ser Leu Arg Leu Ser Val Gly Arg Arg Arg Ala Ser Ser Leu Glu
             35                  40                  45

Val Lys Ala Ser Gly Asn Val Phe Gly Asn Tyr Phe Gln Val Ala Thr
         50                  55                  60

Tyr Gly Glu Ser His Gly Gly Val Gly Cys Val Ile Ser Gly Cys
 65                  70                  75                  80

Pro Pro Arg Ile Pro Leu Thr Glu Ala Asp Met Gln Val Glu Leu Asp
                 85                  90                  95

Arg Arg Arg Pro Gly Gln Ser Arg Ile Thr Thr Pro Arg Lys Glu Thr
                100                 105                 110

Asp Thr Cys Lys Ile Leu Ser Gly Thr His Asp Gly Met Thr Thr Gly
                115                 120                 125

Thr Pro Ile His Val Phe Val Pro Asn Thr Asp Gln Arg Gly Gly Asp
            130                 135                 140

Tyr Ser Glu Met Ser Lys Ala Tyr Arg Pro Ser His Ala Asp Ala Thr
145                 150                 155                 160

Tyr Asp Phe Lys Tyr Gly Val Arg Ala Val Gln Gly Gly Gly Arg Ser
                165                 170                 175

Ser Ala Arg Glu Thr Ile Gly Arg Val Ala Ala Gly Ala Leu Ala Lys
                180                 185                 190

Lys Ile Leu Lys Leu Lys Ser Gly Val Glu Ile Leu Ala Phe Val Ser
            195                 200                 205

Lys Val His Gln Val Val Leu Pro Glu Asp Ala Val Asp Tyr Glu Thr
        210                 215                 220

Val Thr Leu Glu His Ile Glu Ser Asn Ile Val Arg Cys Pro Asp Pro
225                 230                 235                 240

Glu Tyr Ala Glu Lys Met Ile Ala Ala Ile Asp Thr Val Arg Val Arg
                245                 250                 255

Gly Asp Ser Ile Gly Gly Val Val Thr Cys Ile Ala Arg Asn Val Pro
                260                 265                 270

Arg Gly Leu Gly Ser Pro Val Phe Asp Lys Leu Glu Ala Glu Leu Ala
            275                 280                 285

Lys Ala Met Leu Ser Leu Pro Ala Ser Lys Gly Phe Glu Ile Gly Ser
        290                 295                 300
```

```
Gly Phe Ala Gly Thr Asp Phe Thr Gly Ser Glu His Asn Asp Glu Phe
305                 310                 315                 320

Tyr Met Asp Glu Ala Gly Asn Val Arg Thr Arg Thr Asn Arg Ser Gly
            325                 330                 335

Gly Val Gln Gly Gly Ile Ser Asn Gly Glu Ile Ile Tyr Phe Lys Val
        340                 345                 350

Ala Phe Lys Pro Thr Ala Thr Ile Gly Lys Lys Gln Asn Thr Val Ser
    355                 360                 365

Arg Glu His Glu Asp Val Glu Leu Leu Ala Arg Gly Arg His Asp Pro
370                 375                 380

Cys Val Val Pro Arg Ala Val Pro Met Val Glu Ser Met Ala Ala Leu
385                 390                 395                 400

Val Leu Met Asp Gln Leu Met Ala His Ile Ala Gln Cys Glu Met Phe
                405                 410                 415

Pro Leu Asn Leu Ala Leu Gln Glu Pro Ile Gly Ser Ala Ser Ser Ala
            420                 425                 430

Ser Glu Leu Ser Pro Asn Leu Ser
        435                 440

<210> SEQ ID NO 3
<211> LENGTH: 763
<212> TYPE: DNA
<213> ORGANISM: Glycine max

<400> SEQUENCE: 3
gaacaagaac aaatcgctct ggtgggatac agggtggaat tccaatggg gaaatcatta    60 atatgagaat agctttcaag ccaacatcaa caattggaaa gaagcaaaag actgtgactc   120
gagataaaaa agaaacagag tttatagccc gtggtcgcca tgatccttgt gttgtcccaa   180
gagctgtacc tatggtagaa gcaatggtag cttaggttct tgtggaccaa ttgatggcac   240
aatatgcgca gtgtaatctt ttaccaccgtaa actcagattt gcaagaaccc ttggtgccca   300
tactacggcc agaagaagcg ctcctctgaa gaggaagggg gtccataaat cagtaattgg   360
cctttgataa aatcttcctt atggctagtg tttaattgac acggttaatt cactttgatg   420
acaagtccaa gtgaacattg tggcagatat ttttgcgggt gcaatctatc gttttgtatt   480
aatgtaagtt aaactatgtt ttcttttcct ctcttcttct attttcattc tgagggtgaa   540
cattgtttct agtaaacctt gttgcaaaag cagagataga tgtattctta aagtgaactg   600
atattaaaaa ttgtaagaaa cgtatcagtt tttgggctta ataagtgttg ctctgctttg   660
caataaatga agctttggc aactttaaaa aaaaaaaaa aaaaaaaaa aaaaaaaaa       720 aaaaaaaaaa aaaaaaaaa aaaaaaaaaa aaaaaaaaaa aat                       763

<210> SEQ ID NO 4
<211> LENGTH: 108
<212> TYPE: PRT
<213> ORGANISM: Glycine max

<400> SEQUENCE: 4

Thr Arg Thr Asn Arg Ser Gly Gly Ile Gln Gly Gly Ile Ser Asn Gly
 1               5                  10                  15

Glu Ile Ile Asn Met Arg Ile Ala Phe Lys Pro Thr Ser Thr Ile Gly
                20                  25                  30

Lys Lys Gln Lys Thr Val Thr Arg Asp Lys Lys Glu Thr Glu Phe Ile
            35                  40                  45

Ala Arg Gly Arg His Asp Pro Cys Val Val Pro Arg Ala Val Pro Met
```

-continued

```
            50                  55                  60
Val Glu Ala Met Val Ala Leu Val Leu Val Asp Gln Leu Met Ala Gln
 65                  70                  75                  80

Tyr Ala Gln Cys Asn Leu Phe Pro Val Asn Ser Asp Leu Gln Glu Pro
                 85                  90                  95

Leu Val Pro Ile Leu Arg Pro Glu Glu Ala Leu Leu
               100                 105
```

<210> SEQ ID NO 5
<211> LENGTH: 1015
<212> TYPE: DNA
<213> ORGANISM: Triticum aestivum

<400> SEQUENCE: 5

```
gcacgaggct gcaggagctg ttgcaaagaa aattcttaag ctgaaatgtg gagtagagat     60
tctagcattt gtttccaaag tgcatcaagt ggtacttcct gaagacgcag ttgattatga    120
aactcttacc ctggatcaga tagagagcaa catttgtaga tgtcctgatc agaatatgc    180
acagaagatg attgatgcaa ttgataaagt acgagttaat gggaattcga ttggtggggt    240
ggtcacatgc attgccagaa atgttcctcg tgggcttggc tctcctgtat ttgacaaact    300
tgaagctcta ctggcaaagg ctatgctttc tcttcctgca agcaagggt tgagatcgg     360
tagtggattt gcaggtactg acctaactgg aagtgagcat aacgatgagt tctatatgga    420
cgaggctgga aatgtaagaa cacgaaccaa tcgctcgggc ggtgtacagg agggatatc    480
aaatggtgaa actatatact tcaaagtagc tttcaagcca acagcaacta ttgggaagaa    540
gcaaaatact gtaacaaggg atcatgagga tatcgaactt ctgacaaggg gtcgccatga    600
cccatgtgtc gtccctcggg ctgttccaat ggtggagacg atggctgcat ggtcctcat    660
ggaccagctg atggcacatg ttgctcagtg cgagatgttc ccgctgaacc tcgccctaca    720
agaaccaatc ggctccgcaa acagtacacc tgcgttggca ccagatctag catgatgccc    780
gccttggaac gagaaggccc tcttacatat tcttctccct ctctttcatc tgccacattt    840
cagggttttg ctaagcagtt tgcagttttg taccaaacct gtatcctaga atatacattg    900
gattagtgta caccaagaga tctgttgatc accgaaaata aaagtttgcg gcgtgaacag    960
tttgttctgg acaaccagtc aatgtgagca atagaacatt tctccacttg ttgaa         1015
```

<210> SEQ ID NO 6
<211> LENGTH: 257
<212> TYPE: PRT
<213> ORGANISM: Triticum aestivum

<400> SEQUENCE: 6

```
His Glu Ala Ala Gly Ala Val Ala Lys Lys Ile Leu Lys Leu Lys Cys
  1               5                  10                  15

Gly Val Glu Ile Leu Ala Phe Val Ser Lys Val His Gln Val Val Leu
                 20                  25                  30

Pro Glu Asp Ala Val Asp Tyr Glu Thr Leu Thr Leu Asp Gln Ile Glu
             35                  40                  45

Ser Asn Ile Cys Arg Cys Pro Asp Pro Glu Tyr Ala Gln Lys Met Ile
 50                  55                  60

Asp Ala Ile Asp Lys Val Arg Val Asn Gly Asn Ser Ile Gly Gly Val
 65                  70                  75                  80

Val Thr Cys Ile Ala Arg Asn Val Pro Arg Gly Leu Gly Ser Pro Val
                 85                  90                  95
```

```
Phe Asp Lys Leu Glu Ala Leu Leu Ala Lys Ala Met Leu Ser Leu Pro
                100                 105                 110
Ala Ser Lys Gly Phe Glu Ile Gly Ser Gly Phe Ala Gly Thr Asp Leu
            115                 120                 125
Thr Gly Ser Glu His Asn Asp Glu Phe Tyr Met Asp Glu Ala Gly Asn
        130                 135                 140
Val Arg Thr Arg Thr Asn Arg Ser Gly Gly Val Gln Gly Gly Ile Ser
145                 150                 155                 160
Asn Gly Glu Thr Ile Tyr Phe Lys Val Ala Phe Lys Pro Thr Ala Thr
                165                 170                 175
Ile Gly Lys Lys Gln Asn Thr Val Thr Arg Asp His Glu Asp Ile Glu
            180                 185                 190
Leu Leu Thr Arg Gly Arg His Asp Pro Cys Val Val Pro Arg Ala Val
        195                 200                 205
Pro Met Val Glu Thr Met Ala Ala Leu Val Leu Met Asp Gln Leu Met
210                 215                 220
Ala His Val Ala Gln Cys Glu Met Phe Pro Leu Asn Leu Ala Leu Gln
225                 230                 235                 240
Glu Pro Ile Gly Ser Ala Asn Ser Thr Pro Ala Leu Ala Pro Asp Leu
                245                 250                 255
Ala
```

<210> SEQ ID NO 7
<211> LENGTH: 1626
<212> TYPE: DNA
<213> ORGANISM: Zea mays

<400> SEQUENCE: 7

```
gcacgagctc agcttcgtct ctctcgccgg cgcggcaggc aactatcatc acttcattag    60
ctcatccaat ctattccgat gacgaccgtg cccaagccac agcaggtggc gcactcacgg   120
gcacggctcg caccccgcgc gatcggcgcc ttgctggagt ttgccccagc tcctcctcc    180
ctccgcttcg ccgtgcaccg ctgccgcact gctcgcctag aggtgaaggc atctggaaac   240
acgtttggaa actactttca ggttgcaacc tatggtgaat ctcatggggg tggtgttggt   300
tgtgttatca gtggttgtcc acctagaatt ccactcactg aggcagacct acaagttgaa   360
ctcgatcgaa gacggcccgg acagagcaga ataacctcca caaggaagga gactgataca   420
tgcaaaattc tgtcagggac acatgaaggg gtgactactg aacgccaat tcttgttatt    480
gtcccaaaca cagatcaaat aggcagtgat caccgtgaaa tagccaatgt gtaccgacct   540
tctcatgcag acgcaactta tgacttcaag tacggtgtta gagctgtaca gggaggtggg   600
aggtcctcgg gcagaaaaac cgttggaagg gtggctgcag gggccctccc caagaaaatt   660
cttaagctca aatgtggatt agatcttg tcgtttgttt ccaaagtgca tcaggttgtg    720
ctcccagaag acgcggttga ttatgggtct gtaactttgg aacagataga gagcaacatc   780
gttagatgtc ctgatccaga gtacgcagag aagatgatag acgcaatcga cagagtacga   840
gttcgagggg attcggtcgg tggagtgatc acatgcgtcg ctagaaacgt tcctcgcggg   900
ctcggttctc ctgtgttcga caagctcgaa tccgaactgg caaaagctat gctttctatt   960
cctgcgagca acgggttcga gattggcagc ggattcgccg ggaccgactt gacaggaagt  1020
gagcataatg atgagttttta tatggataag gctggaagtg tcaggacacg gactaatcgc  1080
tcgggtggtg tgcagggagg gatatcgaat gttgagattg tgcacttcaa agttgctttt  1140
aagccgacac catctatcgg ggtgaaacag aacaccgtgt caagggagcg tcagaacgtt  1200
```

-continued

```
gagcttctag caagagggcg ccatgaccca tgcgtcgccc ctcgagctgt tcctgtggtg    1260
gaatccatgg ccgcgttggt cctcatggac cagctgatgg cgcacgtggc tcagtgcgag    1320
atgttcgcgc tcaatactgc acttcaagaa ccagttggct ctttctagca gaggcagagc    1380
acacctgatg agctcgcgcc aaattttatc atttatcata gtaataagta gctcaagcgt    1440
ggcttggttt gcttgtctct tgcaccgtag ttttgttttt tttttcccgc aagtgtgatg    1500
cgatgaagtg aataaggcac ttggtttcct gtgcatttgt acacgtttca tataatgtaa    1560
tctacttcga agatgatgca tttttataga tgtggcttgt gaaagacaaa aaaaaaaaa     1620 aaaaaa                                                                1626
```

<210> SEQ ID NO 8
<211> LENGTH: 429
<212> TYPE: PRT
<213> ORGANISM: Zea mays

<400> SEQUENCE: 8

```
Met Thr Thr Val Pro Lys Pro Gln Gln Val Ala His Ser Arg Ala Arg
  1               5                  10                  15

Leu Ala Pro Arg Ala Ile Gly Ala Leu Leu Glu Phe Ala Pro Ala Ser
                 20                  25                  30

Ser Ser Leu Arg Phe Ala Val His Arg Cys Arg Thr Ala Arg Leu Glu
             35                  40                  45

Val Lys Ala Ser Gly Asn Thr Phe Gly Asn Tyr Phe Gln Val Ala Thr
         50                  55                  60

Tyr Gly Glu Ser His Gly Gly Val Gly Cys Val Ile Ser Gly Cys
 65                  70                  75                  80

Pro Pro Arg Ile Pro Leu Thr Glu Ala Asp Leu Gln Val Glu Leu Asp
                 85                  90                  95

Arg Arg Arg Pro Gly Gln Ser Arg Ile Thr Ser Thr Arg Lys Glu Thr
                100                 105                 110

Asp Thr Cys Lys Ile Leu Ser Gly Thr His Glu Gly Val Thr Thr Gly
            115                 120                 125

Thr Pro Ile Leu Val Ile Val Pro Asn Thr Asp Gln Ile Gly Ser Asp
130                 135                 140

His Arg Glu Ile Ala Asn Val Tyr Arg Pro Ser His Ala Asp Ala Thr
145                 150                 155                 160

Tyr Asp Phe Lys Tyr Gly Val Arg Ala Val Gln Gly Gly Gly Arg Ser
                165                 170                 175

Ser Gly Arg Lys Thr Val Gly Arg Val Ala Ala Gly Ala Leu Pro Lys
            180                 185                 190

Lys Ile Leu Lys Leu Lys Cys Gly Leu Glu Ile Leu Ser Phe Val Ser
        195                 200                 205

Lys Val His Gln Val Val Leu Pro Glu Asp Ala Val Asp Tyr Gly Ser
    210                 215                 220

Val Thr Leu Glu Gln Ile Glu Ser Asn Ile Val Arg Cys Pro Asp Pro
225                 230                 235                 240

Glu Tyr Ala Glu Lys Met Ile Asp Ala Ile Asp Arg Val Arg Val Arg
                245                 250                 255

Gly Asp Ser Val Gly Val Ile Thr Cys Val Ala Arg Asn Val Pro
            260                 265                 270

Arg Gly Leu Gly Ser Pro Val Phe Asp Lys Leu Glu Ser Glu Leu Ala
        275                 280                 285
```

-continued

```
Lys Ala Met Leu Ser Ile Pro Ala Ser Asn Gly Phe Glu Ile Gly Ser
    290                 295                 300

Gly Phe Ala Gly Thr Asp Leu Thr Gly Ser Glu His Asn Asp Glu Phe
305                 310                 315                 320

Tyr Met Asp Lys Ala Gly Ser Val Arg Thr Arg Thr Asn Arg Ser Gly
                325                 330                 335

Gly Val Gln Gly Gly Ile Ser Asn Val Glu Ile Val His Phe Lys Val
            340                 345                 350

Ala Phe Lys Pro Thr Pro Ser Ile Gly Val Lys Gln Asn Thr Val Ser
        355                 360                 365

Arg Glu Arg Gln Asn Val Glu Leu Leu Ala Arg Gly Arg His Asp Pro
    370                 375                 380

Cys Val Ala Pro Arg Ala Val Pro Val Val Glu Ser Met Ala Ala Leu
385                 390                 395                 400

Val Leu Met Asp Gln Leu Met Ala His Val Ala Gln Cys Glu Met Phe
                405                 410                 415

Ala Leu Asn Thr Ala Leu Gln Glu Pro Val Gly Ser Phe
            420                 425
```

<210> SEQ ID NO 9
<211> LENGTH: 479
<212> TYPE: DNA
<213> ORGANISM: Oryza sativa
<220> FEATURE:
<221> NAME/KEY: unsure
<222> LOCATION: (243)..(244)
<223> OTHER INFORMATION: n = A, C, G, or T
<220> FEATURE:
<221> NAME/KEY: unsure
<222> LOCATION: (247)
<223> OTHER INFORMATION: n = A, C, G, or T
<220> FEATURE:
<221> NAME/KEY: unsure
<222> LOCATION: (470)
<223> OTHER INFORMATION: n = A, C, G, or T

<400> SEQUENCE: 9

```
tgtatcaaga aacaacatac tgtttcaagg gagcatgagg atgttgaact tttagcaagg      60
ggccgccacg acccatgtgt tgtccctcgc gctgtgccga tggtggagtc catggccgca     120
ttagtcctca tggaccagct gatggcgcac attgctcaat gtgagatgtt tccactgaac     180
cttgctctac aagaaccagt tggctctgcc agcagcgtac ctgcatttgc accagatcta     240
aanngncccc ccctccccc cccccagctt gtttatcatc tatcatattt ctgggttttt      300
ctaaggggtt cgcagttttg ccacaaagcc tgtatcctag tttatatctc gagttattgt     360
acccaaggaa tccgttatac agtgagcatg aagatagaaa tgcgttcatg cgtgttttgt     420
gatatggaca atctgtgctt acatcaagtt attttgagca ataaaaatcn caatttatg      479
```

<210> SEQ ID NO 10
<211> LENGTH: 81
<212> TYPE: PRT
<213> ORGANISM: Oryza sativa

<400> SEQUENCE: 10

```
Cys Ile Lys Lys Gln His Thr Val Ser Arg Glu His Glu Asp Val Glu
  1               5                  10                  15

Leu Leu Ala Arg Gly Arg His Asp Pro Cys Val Val Pro Arg Ala Val
            20                  25                  30

Pro Met Val Glu Ser Met Ala Ala Leu Val Leu Met Asp Gln Leu Met
        35                  40                  45
```

```
Ala His Ile Ala Gln Cys Glu Met Phe Pro Leu Asn Leu Ala Leu Gln
         50                  55                  60

Glu Pro Val Gly Ser Ala Ser Ser Val Pro Ala Phe Ala Pro Asp Leu
 65                  70                  75                  80

Ser
```

<210> SEQ ID NO 11
<211> LENGTH: 966
<212> TYPE: DNA
<213> ORGANISM: Oryza sativa

<400> SEQUENCE: 11

```
cacgagtaca   gcctctcacc   aaccaaacca   acaacctcgc   tccgatggcc   gcgccaacgt    60
cgtcgcagcc   ggtggcgcgc   gtcctccccc   gcggcggcgg   cggcgggttc   cgcgccttcc   120
cggagtccgc   cccggcttcc   ctccgcttct   ccgtcggccg   ccgccgcgcc   gctcgcctag   180
aggtgaaggc   gtctgcaaat   gtatttggga   actacttcca   ggttgcaact   tatggagagt   240
ctcatggagg   cggtgttggt   tgcgtaatca   gtggatgccc   acccagaatc   ccacttactg   300
aagcagatat   gcaagtagaa   ctcgaccgga   gacggccagg   ccagagcaga   ataaccaccc   360
caagaaagga   gactgacact   tgcaaaattc   tttcagggac   acatgaagga   atgaccactg   420
ggacaccaat   tcatgttttt   gtcccgaaca   cagatcagag   agggggtgat   acagtgaaa    480
tggctaaggc   ctacagacct   tcacatgcag   atgcaactta   tgacttcaaa   tacggtgtta   540
gagcagtgca   gggaggtgga   agatcatcag   caagagagac   cattggaagg   gtggctgcag   600
gagctcttgc   aaagaaaatt   cttaagctca   aatctggagt   agagatcttg   gcgtttgtgt   660
ccaaggtgca   tcaagttgta   ctaccagaag   atgccgttga   ttatgacact   gtaacaatgg   720
aacagataga   aagcaacatt   gttagatgtc   ctgatccaga   atatgcacag   aagatgattg   780
atgcactcga   taaagtacga   gttagaggtg   attcgattgg   tggtgtggtc   acatgcattg   840
caagaaatgt   tcctcgtggg   attggctctc   ctgtatttga   caaacttgag   gctgaattgg   900
cgaaagctat   gctttctctt   cctgcaagca   aggggtttga   gatcggcagt   ggatttgtgt   960
tcacta                                                                      966
```

<210> SEQ ID NO 12
<211> LENGTH: 307
<212> TYPE: PRT
<213> ORGANISM: Oryza sativa

<400> SEQUENCE: 12

```
Met Ala Ala Pro Thr Ser Ser Gln Pro Val Ala Arg Val Leu Pro Arg
 1               5                  10                  15

Gly Gly Gly Gly Gly Phe Arg Ala Phe Pro Glu Ser Ala Pro Ala Ser
                 20                  25                  30

Leu Arg Phe Ser Val Gly Arg Arg Ala Ala Arg Leu Glu Val Lys
         35                  40                  45

Ala Ser Ala Asn Val Phe Gly Asn Tyr Phe Gln Val Ala Thr Tyr Gly
         50                  55                  60

Glu Ser His Gly Gly Val Gly Cys Val Ile Ser Gly Cys Pro Pro
 65                  70                  75                  80

Arg Ile Pro Leu Thr Glu Ala Asp Met Gln Val Glu Leu Asp Arg Arg
                 85                  90                  95

Arg Pro Gly Gln Ser Arg Ile Thr Thr Pro Arg Lys Glu Thr Asp Thr
                100                 105                 110
```

-continued

```
Cys Lys Ile Leu Ser Gly Thr His Glu Gly Met Thr Thr Gly Thr Pro
        115                 120                 125
Ile His Val Phe Val Pro Asn Thr Asp Gln Arg Gly Gly Asp Tyr Ser
        130                 135                 140
Glu Met Ala Lys Ala Tyr Arg Pro Ser His Ala Asp Ala Thr Tyr Asp
145                 150                 155                 160
Phe Lys Tyr Gly Val Arg Ala Val Gln Gly Gly Arg Ser Ser Ala
                    165                 170                 175
Arg Glu Thr Ile Gly Arg Val Ala Ala Gly Ala Leu Ala Lys Lys Ile
                180                 185                 190
Leu Lys Leu Lys Ser Gly Val Glu Ile Leu Ala Phe Val Ser Lys Val
        195                 200                 205
His Gln Val Val Leu Pro Glu Asp Ala Val Asp Tyr Asp Thr Val Thr
        210                 215                 220
Met Glu Gln Ile Glu Ser Asn Ile Val Arg Cys Pro Asp Pro Glu Tyr
225                 230                 235                 240
Ala Gln Lys Met Ile Asp Ala Leu Asp Lys Val Arg Val Arg Gly Asp
                    245                 250                 255
Ser Ile Gly Gly Val Val Thr Cys Ile Ala Arg Asn Val Pro Arg Gly
                260                 265                 270
Ile Gly Ser Pro Val Phe Asp Lys Leu Glu Ala Glu Leu Ala Lys Ala
        275                 280                 285
Met Leu Ser Leu Pro Ala Ser Lys Gly Phe Glu Ile Gly Ser Gly Phe
        290                 295                 300
Val Phe Thr
305

<210> SEQ ID NO 13
<211> LENGTH: 541
<212> TYPE: DNA
<213> ORGANISM: Glycine max
<220> FEATURE:
<221> NAME/KEY: unsure
<222> LOCATION: (411)
<223> OTHER INFORMATION: n = A, C, G, or T
<220> FEATURE:
<221> NAME/KEY: unsure
<222> LOCATION: (436)..(437)
<223> OTHER INFORMATION: n = A, C, G, or T
<220> FEATURE:
<221> NAME/KEY: unsure
<222> LOCATION: (448)
<223> OTHER INFORMATION: n = A, C, G, or T
<220> FEATURE:
<221> NAME/KEY: unsure
<222> LOCATION: (466)
<223> OTHER INFORMATION: n = A, C, G, or T
<220> FEATURE:
<221> NAME/KEY: unsure
<222> LOCATION: (473)
<223> OTHER INFORMATION: n = A, C, G, or T
<220> FEATURE:
<221> NAME/KEY: unsure
<222> LOCATION: (479)
<223> OTHER INFORMATION: n = A, C, G, or T
<220> FEATURE:
<221> NAME/KEY: unsure
<222> LOCATION: (500)
<223> OTHER INFORMATION: n = A, C, G, or T
<220> FEATURE:
<221> NAME/KEY: unsure
<222> LOCATION: (504)
<223> OTHER INFORMATION: n = A, C, G, or T
<220> FEATURE:
<221> NAME/KEY: unsure
```

```
<222> LOCATION: (522)
<223> OTHER INFORMATION: n = A, C, G, or T
<220> FEATURE:
<221> NAME/KEY: unsure
<222> LOCATION: (537)
<223> OTHER INFORMATION: n = A, C, G, or T

<400> SEQUENCE: 13
ctcaatcaat ctaattctcc catttctctt ccaatggcgt cttctctttc caccaaacca      60
ttctcagccg acgctctctc cgccttcgct tctctcaatt ccgatctcgg atccctctcc     120
cccgcctacc tccgactctc actccgtcct cgtcttccca agagacttca catacaggcg     180
gctgggagta cctatggaaa tcactttcgt gttacaacat atggggaatc acatggagga     240
ggtgttggtt gtgttattga tggatgtcct cctcgccttc ctctctctga agctgatatg     300
caagtggatc ttgacagaag gaggccaggt cagagccgaa ttacaactcc tagaaaggag     360
actgatacat gtaaaatatt ttcaggagtt tccgaaggaa tcactactgg nactccaatt     420
catgtactgt acccannntac tgatcaanga gggcatgact atagcnagat ggnagtacnt     480
ataggccccc catgcaatgn accntgacat gaactatggg tngatagtta aggtggnggg     540
g                                                                    541

<210> SEQ ID NO 14
<211> LENGTH: 168
<212> TYPE: PRT
<213> ORGANISM: Glycine max
<220> FEATURE:
<221> NAME/KEY: UNSURE
<222> LOCATION: (139)
<223> OTHER INFORMATION: Xaa = ANY AMINO ACID
<220> FEATURE:
<221> NAME/KEY: UNSURE
<222> LOCATION: (164)
<223> OTHER INFORMATION: Xaa = ANY AMINO ACID

<400> SEQUENCE: 14

Met Ala Ser Ser Leu Ser Thr Lys Pro Phe Ser Ala Asp Ala Leu Ser
  1               5                  10                  15

Ala Phe Ala Ser Leu Asn Ser Asp Leu Gly Ser Leu Ser Pro Ala Tyr
                 20                  25                  30

Leu Arg Leu Ser Leu Arg Pro Arg Leu Pro Lys Arg Leu His Ile Gln
             35                  40                  45

Ala Ala Gly Ser Thr Tyr Gly Asn His Phe Arg Val Thr Thr Tyr Gly
         50                  55                  60

Glu Ser His Gly Gly Gly Val Gly Cys Val Ile Asp Gly Cys Pro Pro
 65                  70                  75                  80

Arg Leu Pro Leu Ser Glu Ala Asp Met Gln Val Asp Leu Asp Arg Arg
                 85                  90                  95

Arg Pro Gly Gln Ser Arg Ile Thr Thr Pro Arg Lys Glu Thr Asp Thr
                100                 105                 110

Cys Lys Ile Phe Ser Gly Val Ser Glu Gly Ile Thr Thr Gly Thr Pro
            115                 120                 125

Ile His Val Ser Val Pro Asn Thr Asp Gln Xaa Arg His Asp Tyr Ser
        130                 135                 140

Glu Met Ala Leu Leu Ile Gly Leu His Ala Asn Ala Thr Tyr Asp Met
145                 150                 155                 160

Lys Tyr Gly Xaa Arg Ser Val Lys
                165
```